(12) United States Patent
Walters et al.

(10) Patent No.: US 6,884,231 B1
(45) Date of Patent: Apr. 26, 2005

(54) DUAL CHAMBERED FLUID DISPLACEMENT APPARATUS

(75) Inventors: Rod Mitchell Walters, Reno, NV (US); Chih-Chung Chen, Reno, NV (US)

(73) Assignee: Hamilton Company, Reno, NV (US)

( * ) Notice: Subject to any disclaimer, the term of this patent is extended or adjusted under 35 U.S.C. 154(b) by 90 days.

(21) Appl. No.: 10/273,045

(22) Filed: Oct. 17, 2002

(Under 37 CFR 1.47)

(51) Int. Cl.[7] .................................................. A61M 5/14
(52) U.S. Cl. ........................... 604/82; 604/506; 604/131
(58) Field of Search ................................ 604/131, 506, 604/93.01, 82, 110, 181, 192, 195, 198, 272, 135, 153, 154, 156

(56) References Cited

U.S. PATENT DOCUMENTS

| | | |
|---|---|---|
| 1,135,476 A | 4/1915 | Watts |
| 1,170,958 A | 2/1916 | Butler |
| 1,499,662 A | 7/1924 | Jube |
| 1,850,132 A | 3/1932 | Morse |
| 2,028,161 A | 1/1936 | Mann |
| 2,062,285 A | 12/1936 | Bergman |
| 2,093,344 A | 9/1937 | Wandel |
| 2,410,808 A | 11/1946 | Christensen |
| 3,426,657 A | 2/1969 | Bimba |
| 3,464,359 A | 9/1969 | King et al. |
| 3,735,900 A * | 5/1973 | Gores .......................... 222/129 |
| 4,065,230 A | 12/1977 | Gezari |
| 4,089,624 A | 5/1978 | Nichols et al. |
| 4,242,058 A | 12/1980 | Zakora |
| 4,457,747 A | 7/1984 | Tu |
| 4,481,946 A | 11/1984 | Altshuler et al. |
| 4,486,188 A | 12/1984 | Altshuler et al. |
| 4,695,431 A | 9/1987 | Farrell |
| 4,898,579 A | 2/1990 | Groshong et al. |
| 4,941,808 A | 7/1990 | Qureshi et al. |
| 5,328,459 A | 7/1994 | Laghi |
| 5,366,904 A | 11/1994 | Qureshi et al. |
| 5,407,424 A | 4/1995 | LaFontaine et al. |
| 5,492,535 A | 2/1996 | Reed et al. |
| 5,529,463 A | 6/1996 | Layer et al. |
| 5,540,562 A | 7/1996 | Giter |
| 5,685,846 A * | 11/1997 | Michaels, Jr. ................ 604/90 |

FOREIGN PATENT DOCUMENTS

FR          706280        6/1931

* cited by examiner

*Primary Examiner*—Kevin C. Sirmons
(74) *Attorney, Agent, or Firm*—Bernhard Kreten

(57) ABSTRACT

A dual-chambered dispensing device having a single piston. The device is driven by an electric precision motor. Each chamber is capable of aspiration and dispensation. When one chamber is aspirating, the other is dispensing.

20 Claims, 9 Drawing Sheets

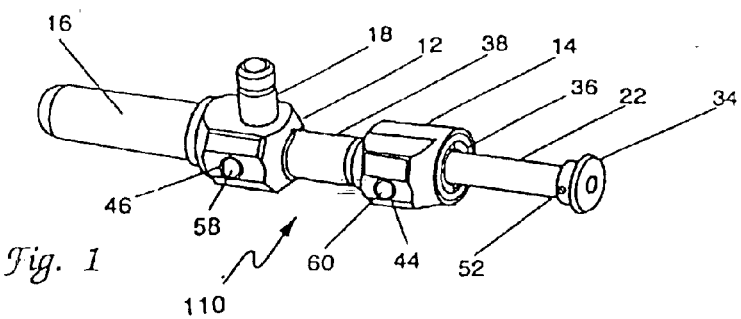
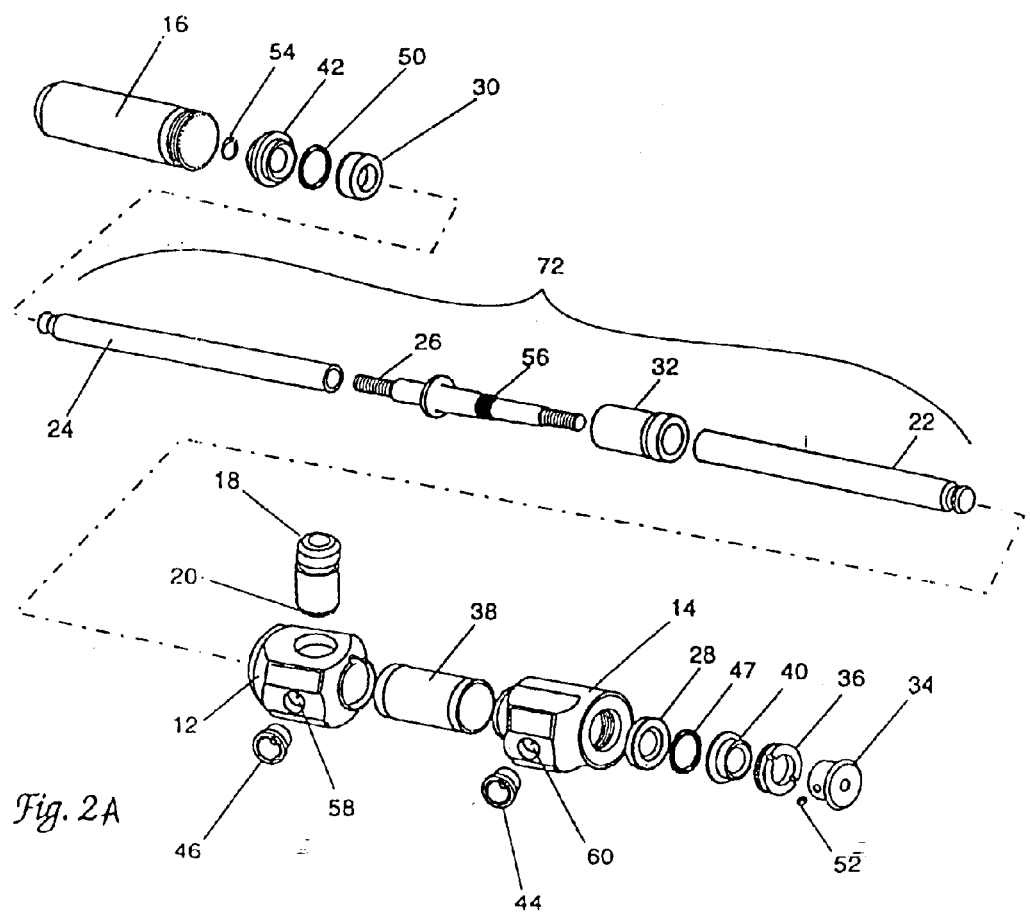

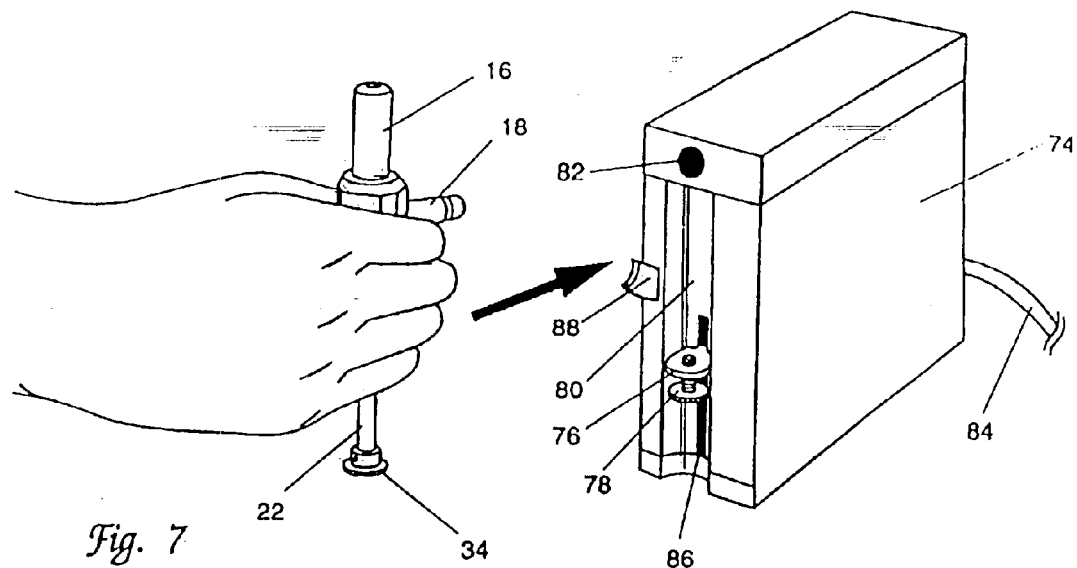
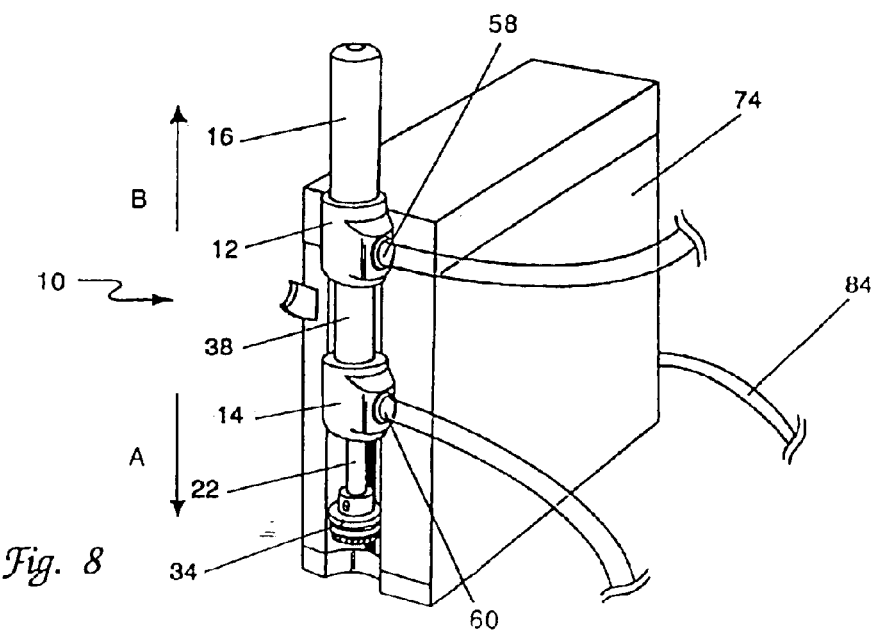

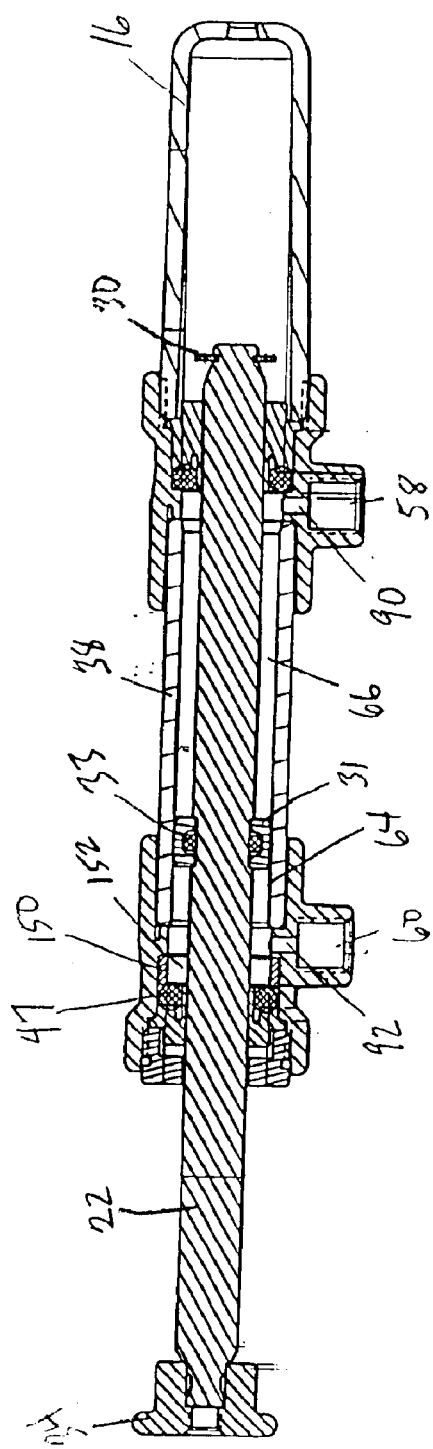
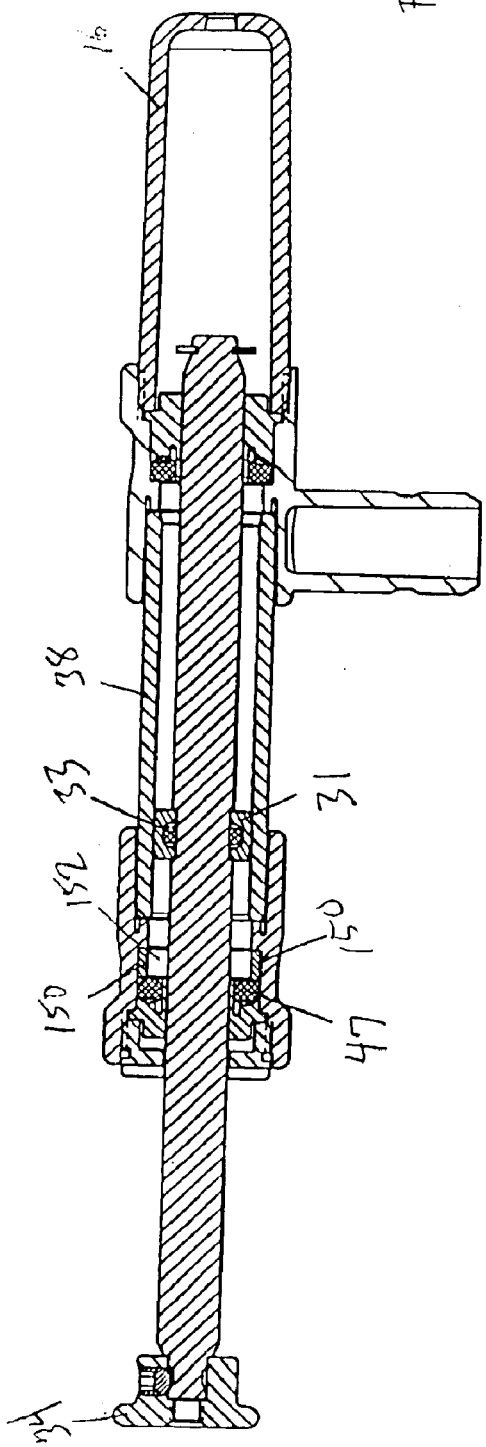

DUAL CHAMBERED FLUID DISPLACEMENT APPARATUS

FIELD OF THE INVENTION

This invention relates to fluid displacement devices. More particularly, this invention relates to single piston, dual chambered fluid displacement devices.

BACKGROUND OF THE INVENTION

Pipetting fluid for chemical analysis has been known for some time. Automated pipetting of fluids is a more recent trend. Automated pipetting includes precision metering of fluids. To aspirate one fluid while simultaneously dispensing another with one single device has been an elusive problem in this field.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| U.S. PATENT DOCUMENTS | | |
|---|---|---|
| U.S. PAT. NO. | ISSUE DATE | INVENTOR |
| 1,135,476 | Apr. 13, 1915 | Watts |
| 1,170,958 | Feb. 8, 1916 | Butler |
| 1,499,662 | Jul. 1, 1924 | Jubé |
| 1,850,132 | Mar. 22, 1932 | Morse |
| 2,028,161 | Jan. 21, 1936 | Mann |
| 2,062,285 | Dec. 1, 1936 | Bergman |
| 2,093,344 | Sep. 14, 1937 | Wandel |
| 2,410,808 | Nov. 12, 1946 | Christensen |
| 3,426,657 | Feb. 11, 1969 | Bimba |
| 3,464,359 | Sep. 2, 1969 | King, et al. |
| 4,065,230 | Dec. 27, 1977 | Gezari |
| 4,089,624 | May 16, 1978 | Nichols, et al. |
| 4,242,058 | Dec. 30, 1980 | Zakora |
| 4,457,747 | Jul. 3, 1984 | Tu |
| 4,481,946 | Nov. 13, 1984 | Altshuler, et al. |
| 4,486,188 | Dec. 4, 1984 | Altshuler, et al. |
| 4,695,431 | Sep. 22, 1987 | Farrell |
| 4,898,579 | Feb. 6, 1990 | Groshong, et al. |
| 4,941,808 | Jul. 17, 1990 | Qureshi, et al. |
| 5,328,459 | Jul. 12, 1994 | Laghi |
| 5,366,904 | Nov. 22, 1994 | Qureshi, et al. |
| 5,407,424 | Apr. 18, 1995 | LaFontaine, et al. |
| 5,492,535 | Feb. 20, 1996 | Reed, et al. |
| 5,529,463 | Jun. 25, 1996 | Layer, et al. |
| 5,540,562 | Jul. 30, 1996 | Giter |

| FOREIGN PATENT DOCUMENTS | | | |
|---|---|---|---|
| PATENT NO. | COUNTRY | PUBLICATION DATE | APPLICANT |
| 706,280 | FR | Jun. 20, 1931 | Denoncourt |

The prior art listed above, but not specifically discussed, teach other devices for pumping or displacing fluids and further catalog the prior art of which the applicant is aware. These references diverge even more starkly from the references specifically distinguished above.

SUMMARY OF THE INVENTION

A device having two chambers for containing fluids and two ports, one port per chamber, is disclosed. This device contains a single piston that may travel through both chambers and a means is provided for sequestering the fluids in the individual chambers. Hence, when the piston is driven through the chambers, one port will aspirate fluid while the other will dispense fluid. These roles will reverse upon the piston traveling in the opposite direction. Significantly, where the chambers are of equal size, any amount aspirated in one chamber will be equal to the amount dispensed from the other.

By coupling the piston to a precise motor driving means, very precise aspiration and dispensation may be achieved. Furthermore, by providing stops on a shaft coupled to the piston, overshooting of the piston can be avoided. By combining these roles in a single device, certain efficiencies are achieved that are desirable in commercial laboratories.

OBJECTS OF THE INVENTION

It is a first object of this invention to provide a device that may simultaneously dispense and aspirate fluids.

It is another object of the present invention to provide a device that will provide such dispensation and aspiration in a precisely metered fashion.

It is another object of the present invention to provide a device that will work in an automated environment.

It is another object of the present invention to minimize the number of parts contained in such invention.

It is another object of the present invention to provide such a device in a plastic molded format to, inter alia, provide cost reduction means.

It is another object of the present invention to provide limit stops on the invention to prevent the invention from overshooting.

It is another object of the present invention to provide equal displacement between the chambers of the invention. That is, that the amount aspirated from one chamber is the same amount being dispensed from the other chamber.

It is yet another object of the present invention to provide a device that is minimal in size so as to facilitate coordination with other such related equipment and enhance ease of movement within a laboratory environment.

Viewed from a first vantage point, it is an object of the present invention to provide a dispenser for preparing samples, comprising, in combination, a syringe having a hollow with a first chamber and a second chamber, the chambers sequestered one from the other by piston means, and means to directly drive the piston means axially through the chambers.

Viewed from a second vantage point, it is an object of the present invention to provide a method for preparing samples, the steps including, connecting a syringe to first and second fluid sources, sequestering the first and second fluids in the syringe into a first and second area, respectively, driving a piston in the syringe to alternatively dispense and receive the fluids in the sequestered areas by a drive motor, and controlling the drive motor.

Viewed from a third vantage point, it is an object of the present invention to provide a dispenser for transferring fluids, comprising, in combination, two shafts, a piston between each shaft, a cylinder provided about the shafts defining two chambers sequestered one from the other by the piston, two seals coupled to the cylinder and about the shafts, one per shaft, wherein the seals are impervious to fluids, and wherein the piston, the seals, the cylinder, and the shafts define two chambers sequestered from each other, and two ports, one per chamber, in fluid communication with the chambers.

These and other objects will be made manifest when considering the following detailed specification when taken in conjunction with the appended drawing figures.

BRIEF DESCRIPTION OF THE DRAWINGS

FIG. 1 depicts one embodiment of the syringe.

FIGS. 2A and 2B are exploded parts views of two distinct embodiments of the syringe.

FIG. 7 depicts the syringe being inserted into the motorized coupling.

FIG. 8 depicts the syringe mounted to the syringe drive unit.

FIGS. 12A and 12B are cross-sectional views of the syringe embodiments that include a spacer.

DESCRIPTION OF PREFERRED EMBODIMENTS

Figure 2B:
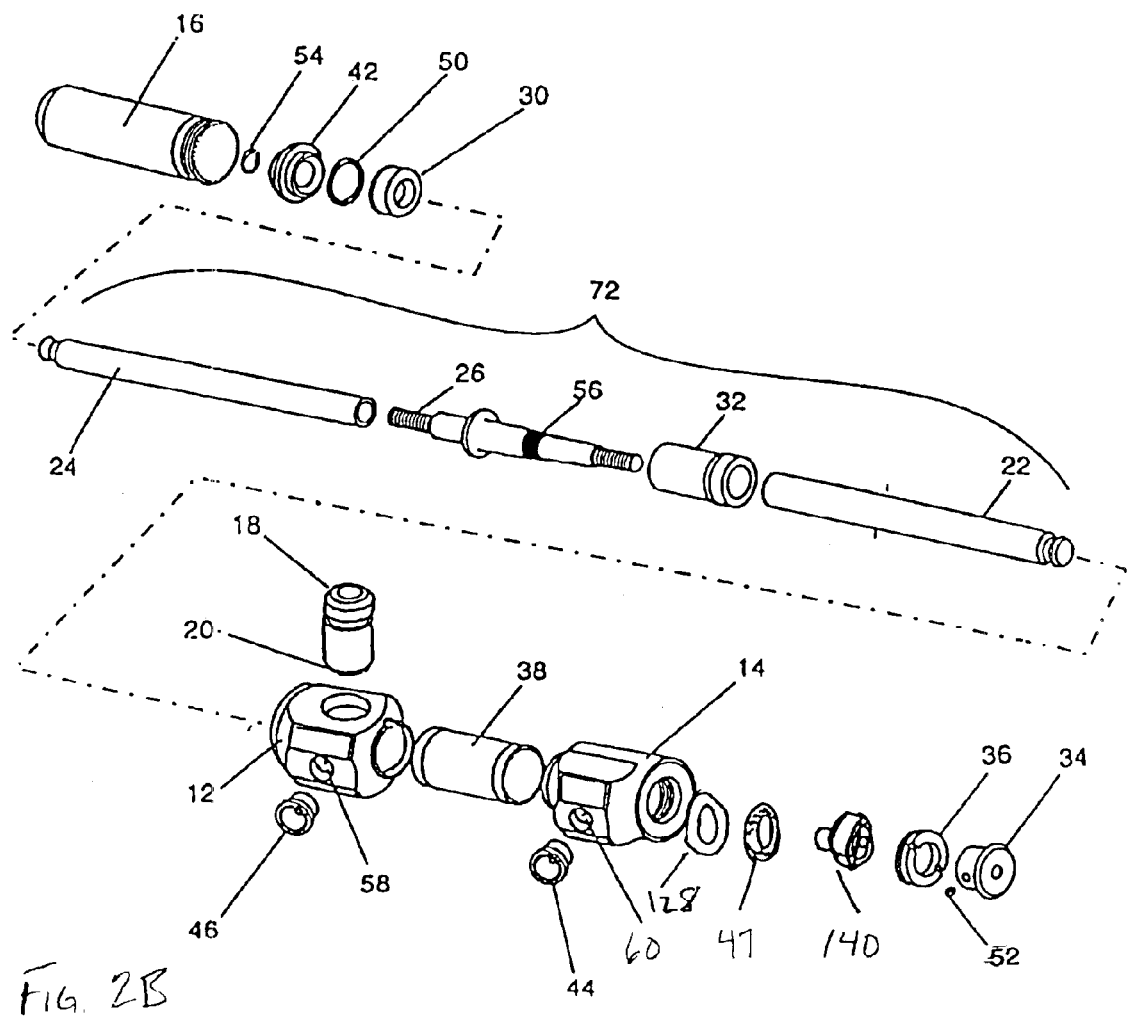

Considering the drawings, wherein like reference numerals denote like parts throughout the various drawing figures, reference numeral 10 is directed to the precision aspiration and dispensation apparatus according to the present invention.

The main components of the invention at hand are as follows: two chambers 64, 66; two ports 58, 60, one port per chamber; and a rod 72, having a piston for sequestering the contents of each said chamber.

Now referring to FIGS. 1 and 2A, an initial embodiment of the invention will be herein described. Syringe 110 consists of an upper housing 12 and a lower housing 14 having a barrel 38 therebetween and a piston rod 72 therethrough. Preferably, the barrel 38 is of a cylindrical shape. Each housing 12, 14 further has located thereon ports 58, 60, one per housing. A cap 16 is coupled to the upper housing 12 to ensconce one end 24 of the piston rod 72. At the other end of the piston rod 72 is coupled a button 34 by means of a set screw 52. A mounting post 18 is further provided on upper housing 12 and coupled by weld area 20 to mate with a mounting bore 82 on a syringe drive unit for motor housing 74 (as depicted in FIGS. 7 and 8).

The piston rod 72 itself may be comprised of several components. On smaller syringes, an upper shaft 24 and a lower shaft 22 are coupled to a shaft insert 26. On larger syringes, the rod 72 is one piece. Shaft insert 26 also has thereon an O-ring 56 for slideably receiving a plunger tip 32 thereon. The combination of the plunger tip 32, shaft insert 26 and O-ring 56, as depicted, together comprise what may better be described as a piston to inhibit fluids in one chamber from gaining access to another chamber.

A stop is also provided in the form of E-ring 54 on a terminal end of the upper shaft 24. The upper shaft 24 passes through the housing 12, which contains an upper seal 30, upper O-ring 50, upper bearing 42, and cap 16. Such stop prohibits upper shaft 24 from axially sliding too far within upper housing 12. Similarly, lower shaft 22 passes through, at its terminal end, a lower seal 28, O-ring 47, lower bearing 40, and end 36 contained in housing 14. The shaft has at its end the previously described button 34.

Each port 58, 60 is able to accomplish the double duty of aspiration and dispensation.

FIG. 2B depicts a second embodiment of the invention. In this embodiment, lower seal 28 is replaced by back-up ring 128 and lower bearing 40 is replaced by a seal/bearing combination 140. O-ring 47 sits between back-up ring 128 and seal/bearing 140.

Figure 3:
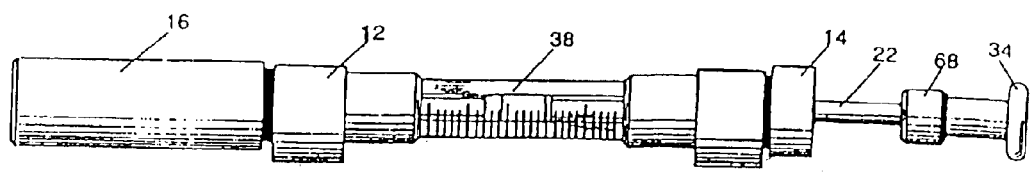
FIG. 3 depicts another embodiment of the syringe.
Figure 4:
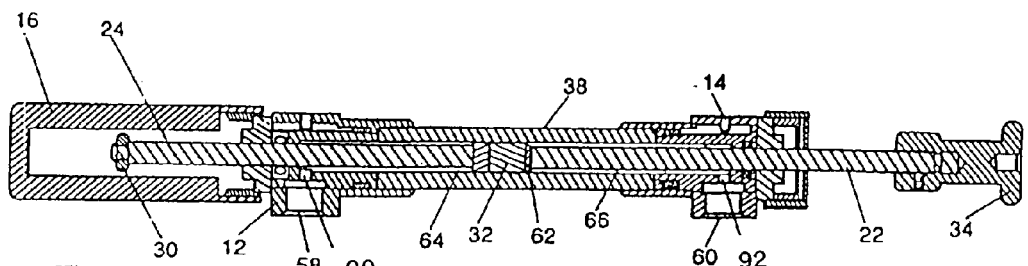
FIG. 4 is a cross-sectional view of the syringe of FIG. 3.

Referring now to FIGS. 3 and 4, another embodiment is depicted with the following variations. Button 34 has taken on a new shape to better fit and form for manipulation by syringe drive unit 74. Barrel 38 is transparent or semi-transparent with hash marks optionally thereon to allow visible assurity.

As can be particularly seen in FIG. 4, fluids passing though ports 58, 60 will then pass through channels 90, 92, respectively, and thereafter into upper chamber 64 and lower chamber 66. The upper chamber 64 and lower chamber 66 are defined by that space not occupied by piston rod 72, or more particularly, upper shaft 24, lower shaft 22, plunger tip 32, and tip stop 62. Clearly, by varying the size of the barrel 38 or the size of the upper shaft 24 or lower shaft 22, the volumes of chambers 64, 66 may be varied.

Figure 5:
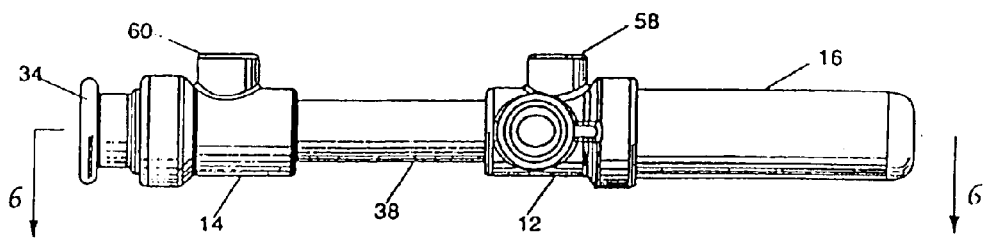
FIG. 5 depicts a preferred embodiment of the syringe.
Figure 6:
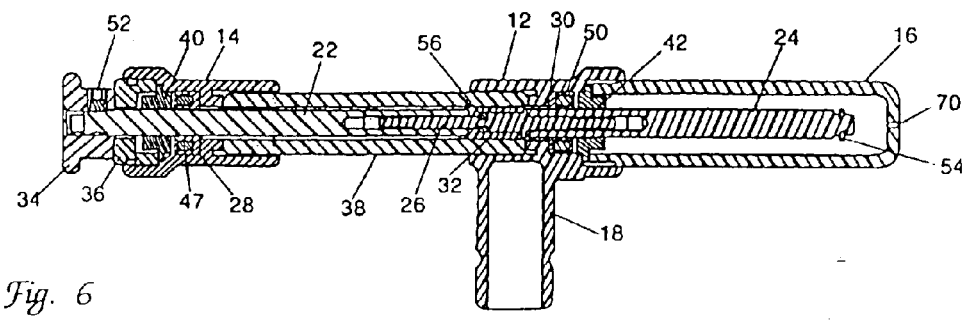
FIG. 6 is a cross-sectional view of the syringe of FIG. 5 taken along line 6—6.

As further depicted in FIGS. 5 and 6, a preferred embodiment is shown made of an economically mass produceable material, such as plastic, wherein certain parts have been combined or eliminated for efficiency purposes and to reduce costs. In particular, and as can be seen in FIG. 6, shaft insert 26 is a variation for this embodiment for easier insertion and manipulation. Vent 70 has been added to allow venting of air as piston rod 72 travels within cap 16. As can also be seen, many items have been molded together to form single components instead of multiple components.

FIGS. 7 through 10 include syringe drive unit 74. In particular, FIG. 7 shows syringe 110 being mated with syringe drive unit 74 within syringe relief 80. As shown, mounting bore 82 will receive mount 18 and piston agitation surface 76 will receive button 34, coupleable by button coupling means 78 into button 34. Release lever 88 is also provided to so release mount 18 from bore 82 as needed by expanding biased ring 106 when release lever 88 is depressed. Biased ring 106 is normally biased inward within bore 82 to hold fast a mount 18. By pressing release lever 88 toward syringe drive unit 74, release arm 104 arcs toward arrow R and likewise causes biased ring release 120 to pull biased ring 106 outward. Due to spring 102 connected to release arm 104, when one frees the release lever 88, the bias of spring 102 causes release lever 88 to again project outward and bias ring 106 to constrict within mounting bore 82.

As shown in FIG. 8, syringe 110 is coupled to housing 74 to so comprise the invention 10.

Figure 9:
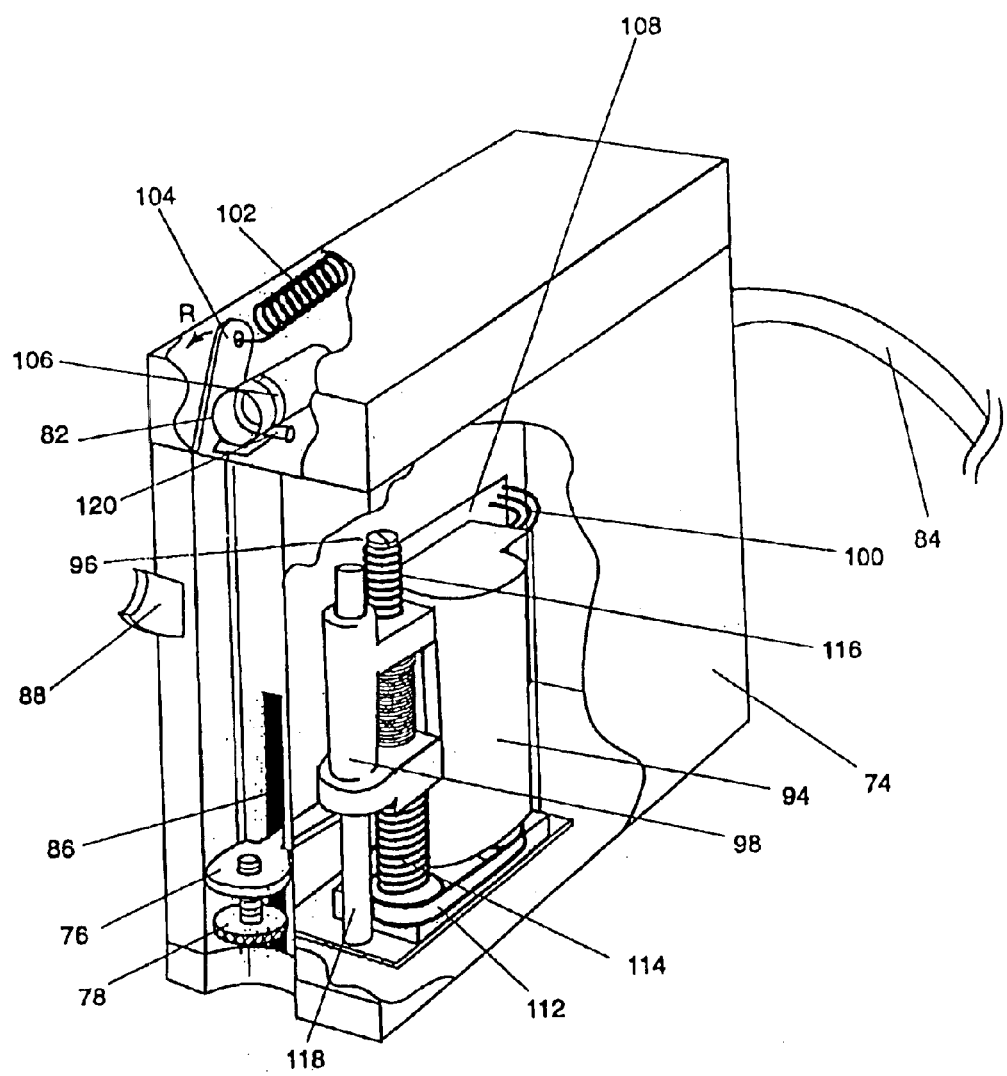
FIG. 9 is a cutaway perspective view of the syringe drive unit depicting the insides thereof including motor and gears.
Figure 10:
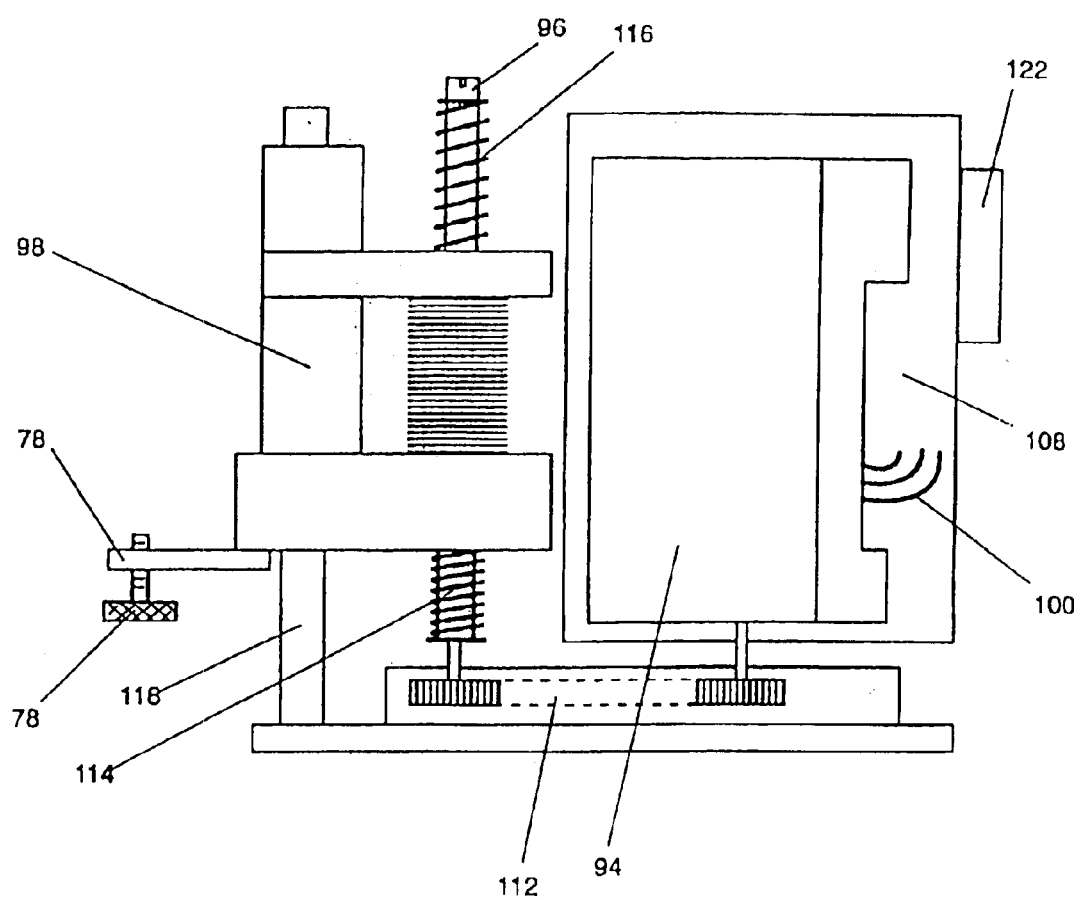
FIG. 10 is a front view of the circuit components with the syringe drive unit.
Figure 11:
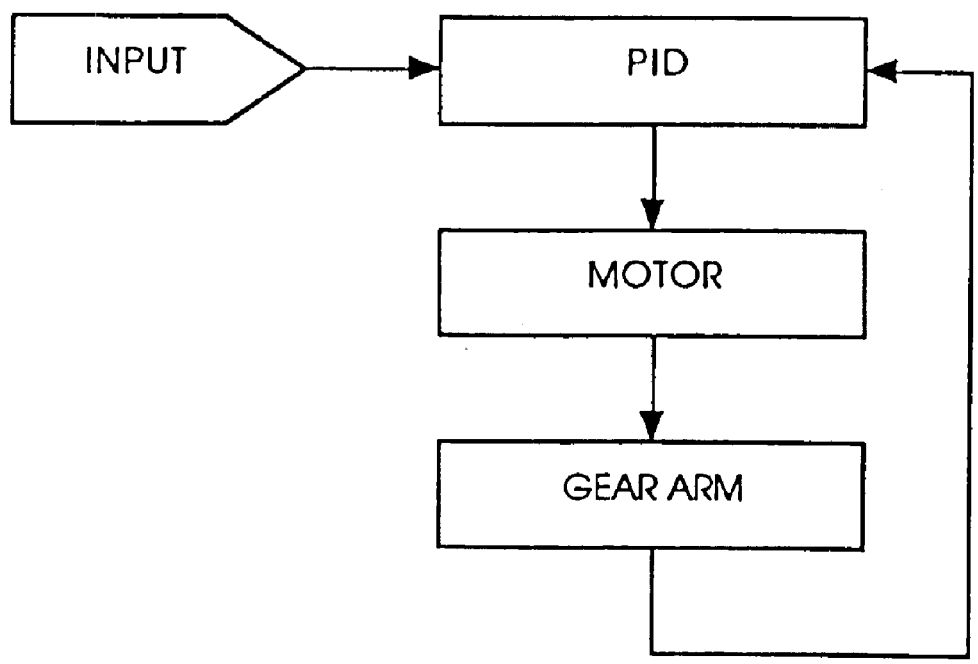
FIG. 11 is a schematic depiction of the circuit of the syringe drive unit.

FIG. 9 shows in cutaway the drive mechanism for the precision piston agitation surface. Included therein are a motor 94, preferably a DC servomotor, and an elongated worm gear 96, wherein a belt 112 couples the motor to the gear. A carriage 98 is carried upon gear 96 and also upon a guide 118. As the worm gear 96 turns, the carriage 98 may move upwardly or downwardly. Coupled to the carriage is the piston agitation surface 76 which would likewise move upwardly or downwardly with the carriage. Also included upon the worm gear are a lower spring restraint 114 and an upper spring restraint 116. The springs may act against the action of the motor gearing to preclude drift of the carriage upwardly or downwardly. To control the motor 94 is a circuit board 108 containing a PID programmable microprocessor thereon. Wires 100 extending from motor 94 are coupled to and circuitously engaged with circuit board 108. Circuit board 108 additionally has an interface 122 which may couple to a user interface such as a keyboard or computer. Interface 122 may be of any variety of interfaces capable of carrying signals such as a serial or parallel interface. The flow diagram of FIG. 11 further depicts schematically the circuit described hereinabove.

In use and operation (FIG. 8), when a piston rod 72 is fully inserted within chambers 64, 66, withdrawing piston rod 72 axially from those chambers along arrow A will result in fluid being dispensed from chamber 66 through port 60 and fluid being aspirated into chamber 64 through port 58. Thereafter, pushing that same piston rod 72 in the opposite direction along arrow B will cause the opposite result, that is, aspiration via port 60 and dispensation via port 58. Of course, the length of the stroke of piston rod 72 will be proportional to the amounts aspirated and dispensed from the chambers. Therefore, by utilizing motor 94 precisely, very specific amounts of fluid can be dispensed and aspirated simultaneously. This can readily be accomplished by a number of motors, especially an appropriately configured DC servomotor, as will now be evident to those having ordinary skill in the art, informed by the present disclosure.

Additionally, by coupling the syringe drive unit 74 to a computer control means, such as a microprocessor within said drive unit, even more precise metering can be accomplished in plunging and extracting the piston 72.

FIGS. 12A and 12B show another embodiment of the invention, in which an annular spacer 150 has been inserted in the end of the syringe having the button 34 (rather than that having the cap 16). The spacer is located inboard of and adjacent to O-ring 47. The spacer 150 creates a pocket 152 in which fluid pools, which keeps the area lubricated and increases the longevity of the instrument. The plunger tip 32 and O-ring 56 assembly is replaced by a combination of wipers 31 and O-rings 33.

Figure 13:
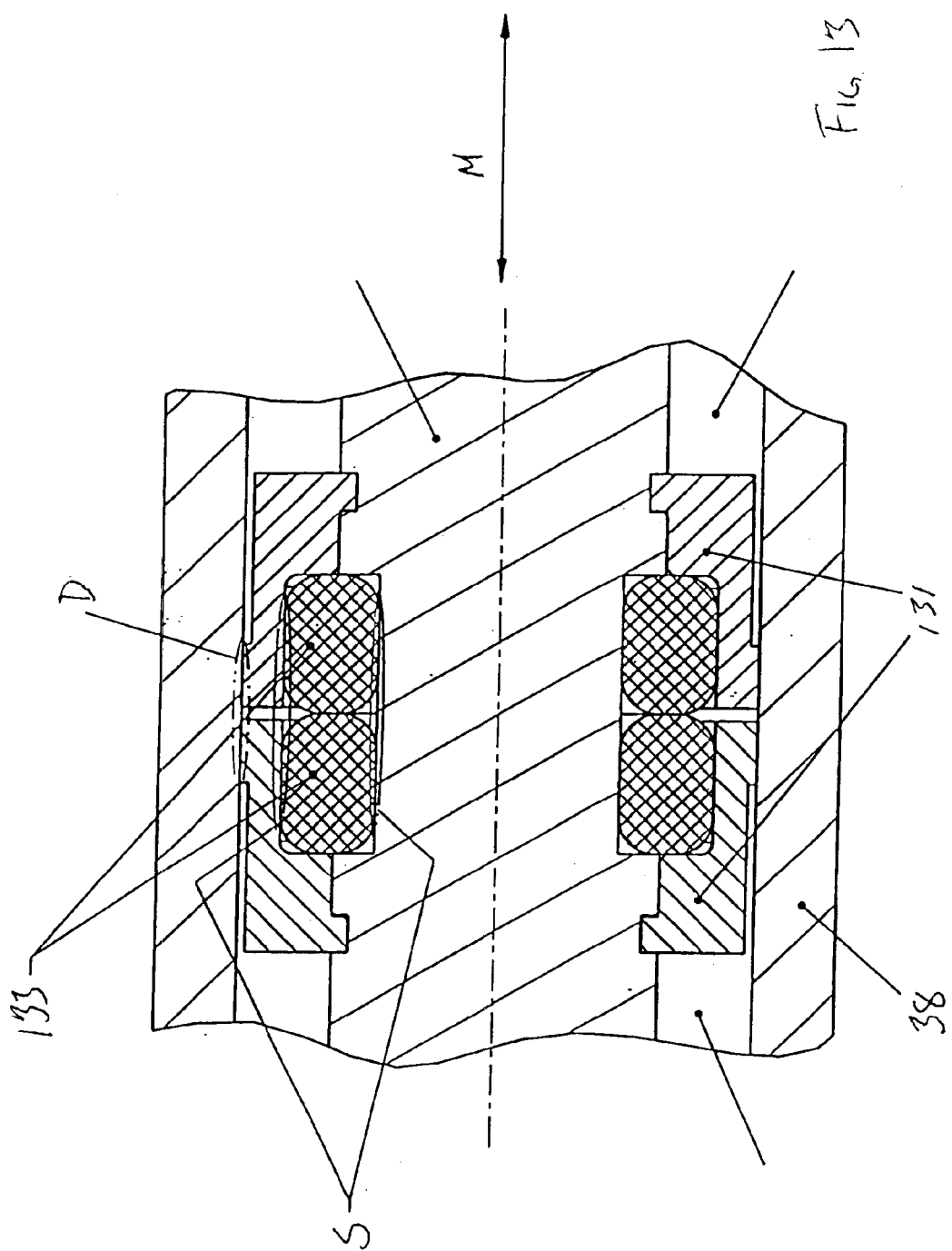
FIG. 13 is a cross-sectional view of an alternative plunger tip.

FIG. 13 depicts another combination that replaces the plunger tip 32 and O-ring 56 assembly, which utilizes two O-rings 133. The O-rings 133 are located on the shaft insert 126 and are separated from the barrel 38 by a pair of wipers 131. The combination of these elements (in all embodiments of FIGS. 12A,12B,13) produces static seals S and dynamic seals D (as the shaft moves along arrow M) to prevent fluid leakage and additionally prolong the life of the instrument.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A dispenser for preparing samples, comprising, in combination:
    a syringe having a hollow interior with a first chamber and a second chamber, said chambers sequestered one from the other by piston means, wherein said piston means comprises a first shaft and a second shaft coupled together and having said slideably mountable cylinder therebetween, said syringe further comprising a plurality of ports wherein said ports are in communicable contact with said hollow, and wherein said chambers are sequestered by means of a slideably mountable cylinder having a channel therethrough for resiliently coupling to said piston means; and
    means to directly drive said piston means axially through said chambers.

2. The dispenser of claim 1 wherein said second shaft includes a seal means and spacer means adjacent said seal means.

3. The dispenser of claim 2 further comprising a stop coupled to a free end of said first shaft for limiting said piston axial movement.

4. The dispenser of claim 3 further comprising a mounting means coupled to an exterior of said syringe.

5. The dispenser of claim 4 further comprising button means coupled to a free end of said second shaft.

6. The dispenser of claim 5 wherein said means to drive said piston comprises:
    a housing;
    a motor within said housing;
    means on said housing for coupleably receiving said mounting means;
    means to couple said button means to a pumping arm, said pumping arm coupled to said motor; and
    electric power means for said motor.

7. The dispenser of claim 6 wherein said motor is a DC servomotor.

8. The dispenser of claim 7 further comprising a tubular cap closed at one end and open at another end, said open end capable of receiving and enshrouding said free end of said first shaft therein, and wherein said tubular cap open end is coupled to said syringe.

9. A method for preparing samples, the steps including:
    connecting a syringe to first and second fluid sources;
    sequestering the first and second fluids in the syringe into a first and second area, respectively;
    driving a piston in the syringe to alternatively dispense and receive the fluids in the sequestered areas by a drive motor; and
    controlling the drive motor.

10. A dispenser for transferring fluids, comprising, in combination:
    two shafts;
    a piston between each said shaft;
    a cylinder provided about said shafts defining two chambers sequestered one from the other by said piston;
    two seals coupled to said cylinder and about said shafts, one per shaft, wherein said seals are impervious to fluids, and wherein said piston, said seals, said cylinder, and said shafts define two chambers sequestered from each other; and
    two ports, one per chamber, in fluid communication with said chambers.

11. The dispenser of claim 10 wherein said chambers are equal in volume.

12. The dispenser of claim 11 further comprising a button coupled to the terminal end of one shaft remote from said piston and a stop coupled to the terminal end of said other shaft remote from said piston.

13. The dispenser of claim 12 further comprising a cap coupled to the end of said cylinder corresponding to said stop-end of said shaft, said cap consisting of a cylindrically formed tube, open at one end and closed at the other, wherein said open end is coupled to said cylinder.

14. The dispenser of claim 13 further comprising a vent, said vent consisting of a passage through said cap.

15. The dispenser of claim 14 further comprising a mounting means coupled to an exterior of said cylinder.

16. The dispenser of claim 15 further comprising a motor housing for receiving said cylinder and mounting means.

17. The dispenser of claim 16 further comprising an electrical precision motor means within said housing.

18. The dispenser of claim 17 further comprising piston agitation means protruding from said housing coupleable to said button and driven by said motor means for pumping said shafts and piston within said cylinder.

19. A dispenser for preparing samples, comprising, in combination:

a syringe having a hollow interior with a first chamber and a second chamber, said chambers sequestered one from the other by piston means, and wherein said chambers are sequestered by means of a plurality of seals and a plurality of wipers coupling to said piston means, said syringe further comprising a plurality of ports wherein said ports are in communicable contact with said hollow, and wherein said chambers are sequestered by means of a slideably mountable cylinder having a channel therethrough for resiliently coupling to said piston means; and means to directly drive said piston means axially through said chambers.

20. The dispenser of claim 19 wherein said plurality of wipers encircle said plurality of seals about said piston means, wherein said wipers form a static seal with said plurality of seals and a dynamic seal with an interior surface of said hollow in said syringe.

* * * * *